United States Patent [19]
Galando

[11] Patent Number: 5,475,730
[45] Date of Patent: Dec. 12, 1995

[54] TELESCOPING X-RAY SUPPORT ARMS

[75] Inventor: John Galando, Bellevue, Wash.

[73] Assignee: John K. Grady, Harvard, Mass.

[21] Appl. No.: 295,526

[22] Filed: Aug. 24, 1994

[51] Int. Cl.⁶ .................................................... A61B 6/00
[52] U.S. Cl. .......................... 378/157; 378/193; 378/198
[58] Field of Search .................................... 378/193, 195, 378/196, 197, 198, 167

[56] References Cited

U.S. PATENT DOCUMENTS

| 4,716,581 | 12/1987 | Barud | 378/197 X |
| 4,866,751 | 9/1989 | Louiday | 378/197 X |
| 4,868,845 | 9/1989 | Koropp | 378/197 X |
| 4,872,192 | 10/1989 | Hahn et al. | 378/197 X |

FOREIGN PATENT DOCUMENTS 3251230  11/1991  Japan ...................................... 378/198

*Primary Examiner*—David P. Porta
*Attorney, Agent, or Firm*—James H. Grover

[57] ABSTRACT

X-ray apparatus carrying an X-ray tube as a source and an image intensifier as a receptor on opposite ends of a two-limbed C-Arm has a horizontal support arm extending from a base to a vertical support arm for the C-arm. The vertical arm has a plurality of telescoping tubular sections which can be extended or contracted along a vertical axis to raise or lower the C-arm relative to the level of the base. The horizontal arm also extends telescopingly to increase the space between the base and C-arm to give free passage of medical personnel through the space, the base having a height sufficient to hold the horizontal arm above a moderately tall operator. The horizontal arm is pivoted on a vertical axis through the base to swing the C-arm, X-ray tube and image intensifier over a patient table in coordination with extension of the horizontal arm or rotation of the vertical arm sections to scan the X-ray tube and receptor over a large area of the patient table. All movements may be manual or motorized. The X-ray apparatus and patient table may be fixed or mobile.

18 Claims, 1 Drawing Sheet

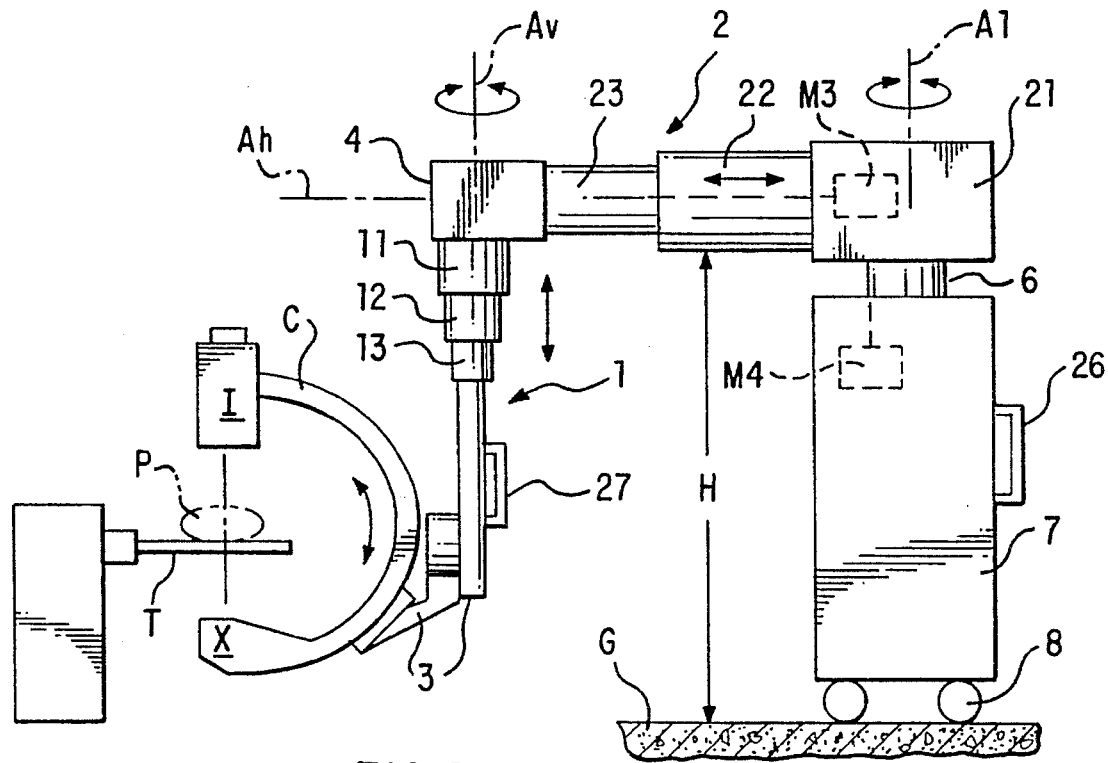
FIG. 1
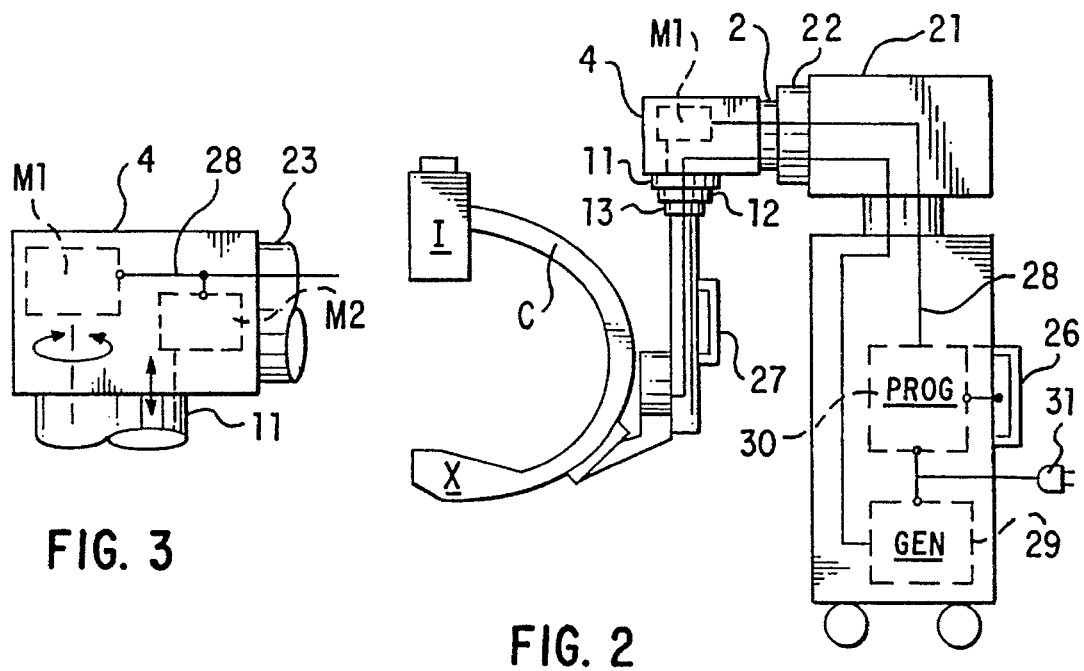
FIG. 3
FIG. 2

TELESCOPING X-RAY SUPPORT ARMS

BACKGROUND OF THE INVENTION

This invention relates to X-ray apparatus in which the X-ray source and X-ray receptor are held at opposite ends of a two-limbed support, the support itself being mounted on arms extending from a base, and has for its object to provide a compact, self contained, mobile unit which can be moved from one hospital room to another and plugged into a power outlet where it is to be used. Further objects are to provide support arms which allow the unit to be compressed for moving, and which afford greater accessibility for the medical operator of the unit and the ability to scan large areas of a patient freely.

SUMMARY OF THE INVENTION

According to the invention X-ray apparatus for examination of a patient comprises an upright base, a two-limbed support with a X-radiation source on one limb and an X-radiation receptor on the other limb. A horizontal support arm extending from the base; and a vertical support arm extending from the horizontal arm to the two-limbed support. The vertical support includes a plurality of telescoping tubular sections extendible under motor drive along a vertical axis so as to lower the two-limbed support and the X-radiation source and receptor relative to the base. The vertical arm may also be rotated by a second motor. Preferably the horizontal arm is driven telescopically along a horizontal axis to move the radiation source and receptor away from the base providing room for a medical operator, and toward the base for compaction and moving.

DRAWINGS

FIGS. 1 and 2 are side elevations of X-ray apparatus according to the invention respectively in extended and compacted form; and FIG. 3 is an enlarged detail of the apparatus.

DESCRIPTION

The X-ray apparatus in the figures comprises a C-arm C carrying an X-ray source X and an X-ray receptor such as an image intensifier I at its opposite ends. Sliding movement of the C-arm rotates the X-ray source and receptor around a patient P on a table T as described in detail in U.S. Pat. No. 5,052,036.

The C-arm is supported at the patient table by a vertical arm 1 and a horizontal arm 2. The lower end of the vertical arm 1 mounts the C-arm on a bracket 3. The upper end of the vertical arm is connected to a housing 4 at one end of the horizontal arm 2. The other end 21 of the horizontal arm is rotatively mounted on a shaft 6 rotating around a vertical axis A1 through a supporting base or cart 7 on wheels 8.

According to one aspect of the invention the vertical arm 1 is formed by tubular sections 11, 12 and 13 telescoping on a vertical axis Av. When driven by a first motor M1 mounted in the housing 4 the telescoping sections are extended from a compact position shown in FIG. 2, to an expanded position shown in FIG. 1 thereby to lower the two-limbed C-arm and the radiation source X and receptor R vertically relative to the wheeled base.

Further the uppermost section 11 of the vertical arm is journalled in the housing 4 at the end of the horizontal arm 2 to allow the vertical arm to rotate about the vertical axis Av when turned by a second motor M2 mounted in the housing. This rotation of the vertical shaft swings the X-ray source and receptor across the patient table T.

Similarly, the horizontal arm 2 is comprised of telescoping, tubular sections 21, 22 and 23 which allow the horizontal arm to be extended or contracted along a horizontal axis Ah when reciprocated by a third motor M3 in the section 21. Swinging the vertical arm 1 around the vertical axis Av in simultaneous coordination with extension of the horizontal arm 2 will move the X-ray source and receptor on a straight line over the patient table T. Similar coordination of rotation of the horizontal arm about a first axis A1 through its end section 21 by a fourth motor M4 in the base, if coordinated with extension of the horizontal arm by the third motor M3, will guide the radiation source and receptor over a substantially larger area of the patient table. Low friction joints between the sections of the arms and the base permit these movements to be effected manually.

The motors M1, M2 and M3 driving the reciprocating and rotary motions of the vertical arm 1 and the reciprocating motion of the horizontal arm 2 are electrically controlled by either of two switch or controlling panels 26 on the wheeled base 7 or 27 on the vertical arm 1. FIGS. 2 and 3 shows wiring 28 exemplary of connections between the base control panel 26, through a computer or programmer 30 to the first and second motors M1 and M2. Because the telescoping sections of the vertical and horizontal arms are tubular, the wiring connections can be run internally of the support arms. A generator supplies high voltage through a cable 30 to the X-ray source, for example a tube. Power for all the electrical units can be supplied from a conventional plug 31.

The height of the wheeled base 7 is selected so as to accommodate passage of a moderately tall medical operator in the space H between the ground G and the horizontal arm 2 when that arm is extended. Yet the vertical and horizontal arms 1 and 2 can be retracted to the compact condition of FIG. 2 for rolling movement of the X-ray apparatus through doors from room to room of a hospital. The table may be fixed or moveable with the X-ray apparatus.

I claim:

1. X-ray apparatus for examination of a patient comprising:

an upright base;

a two-limbed support with a X-radiation source on one limb and an X-radiation receptor on the other limb;

a horizontal support arm extending from the base; and a vertical support arm extending from the horizontal arm to the two-limbed support including a plurality of telescoping tubular sections extendible along a vertical axis to lower the two-limbed support and the X-radiation source and receptor relative to the base.

2. Apparatus according to claim 1 wherein the vertical support arm is rotatable about the vertical axis to swing the X-radiation source and receptor about the axis.

3. Apparatus according to claim 1 including first motor means to drive the vertical arm along the vertical axis.

4. Apparatus according to claim 3 including second motor means to rotate the vertical arm about the vertical axis.

5. Apparatus according to claim 4 including control means on the vertical arm for energizing the first motor means.

6. Apparatus according to claim 1 wherein the horizontal support arm comprises a plurality of tubular telescoping sections extendible along a horizontal axis to extend the radiation source and receptor away from the base.

7. Apparatus according to claim 2 wherein the horizontal support arm comprises a plurality of tubular telescoping sections extendible along a horizontal axis to extend the radiation source and receptor away from the base simultaneously with swinging of the source and receptor about the vertical axis, so as to move the source and receptor along a straight line.

8. Apparatus according to claim 7 including third motor means to extend the horizontal arm along the horizontal axis.

9. Apparatus according to claim 1 wherein the base is of a height to hold the horizontal arm above an operator so as to permit passage of the operator between the base and vertical arm when the horizontal arm is extended.

10. Apparatus according to claim 3 including electric wiring through the tubular horizontal and vertical arms to the first motor means.

11. Apparatus according to claim 3 including a control switch on the vertical arm connected to the first motor means.

12. Apparatus according to claim 3 including a control switch on the vertical arm connected to the first motor means, the switch being readily accessible to the operator when the horizontal arm is extended.

13. Apparatus according to claim 1 wherein the horizontal arm is pivotally mounted on the base for rotation about a vertical axis parallel to the vertical axis of the vertical arm.

14. Apparatus according to claim 6 wherein the horizontal arm is pivotally mounted on the base for rotation about a vertical axis parallel to the vertical axis of the vertical arm so that the X-radiation source and receptor can be guided over a substantial area of examination.

15. Apparatus according to claim 1 wherein the base is mobile on rolling means.

16. Apparatus according to claim 1 wherein the base and two-limbed support are electrically connected through the horizontal and vertical support arms.

17. Apparatus according to claim 6 wherein the base and two-limbed support are electrically connected through the horizontal and vertical support arms.

18. Apparatus according to claim 1 in combination with a patient table.

\* \* \* \* \*